(12) United States Patent
Kintzig et al.

(10) Patent No.: US 6,379,317 B1
(45) Date of Patent: Apr. 30, 2002

(54) ANALYTICAL MEASURING DEVICE WITH LANCING DEVICE

(76) Inventors: Hans Kintzig, In der Muld 4, D-67311 Tiefenthal; Michael Schabbach, Lettengasse 4, D-69493 Hirschberg; Hans-Ruediger Murawski, Carl-Lepper-Strasse 10, D-68623 Lampertheim; Wolfgang Obermeier, Kepplerstrasse 19, D-69120 Heidelberg; Karl Miltner, Ernst-Ludwig-Kirchner-Strasse 22, D-67227 Frankenthal, all of (DE)

( * ) Notice: Subject to any disclaimer, the term of this patent is extended or adjusted under 35 U.S.C. 154(b) by 0 days.

(21) Appl. No.: 09/555,205
(22) PCT Filed: Nov. 30, 1998
(86) PCT No.: PCT/EP98/07706
§ 371 Date: May 25, 2000
§ 102(e) Date: May 25, 2000
(87) PCT Pub. No.: WO99/27854
PCT Pub. Date: Jun. 10, 1999

(30) Foreign Application Priority Data

Nov. 28, 1997 (DE) .......................................... 197 52 688
May 29, 1998 (DE) .......................................... 198 24 036

(51) Int. Cl.⁷ .............................. A61B 5/14; A61B 5/00
(52) U.S. Cl. ...................... 600/573; 600/584; 600/309
(58) Field of Search ................................. 600/308, 309, 600/316, 322, 341, 345, 347, 365, 368, 573, 576, 583, 584; 606/181, 182

(56) References Cited

U.S. PATENT DOCUMENTS

| | | | | |
|---|---|---|---|---|
| 4,787,398 A | * | 11/1988 | Garcia et al. ................ | 600/583 |
| 4,790,979 A | * | 12/1988 | Terminello et al. ......... | 600/583 |
| 4,995,402 A | * | 2/1991 | Smith et al. ................. | 600/584 |
| 5,066,859 A | * | 11/1991 | Karkar et al. ................ | 600/326 |
| 5,279,294 A | * | 1/1994 | Anderson et al. ........... | 600/583 |
| 5,628,309 A | * | 5/1997 | Brown ......................... | 600/310 |
| 5,951,492 A | * | 9/1999 | Douglas et al. .............. | 600/583 |
| 5,971,941 A | * | 10/1999 | Simons et al. ............... | 600/583 |

* cited by examiner

Primary Examiner—Kevin Shaver
Assistant Examiner—Charles Marmor, II
(74) Attorney, Agent, or Firm—Brinks Hofer Gilson & Lione

(57) ABSTRACT

The invention concerns-a system for determining the presence or the content of an analyte in blood comprising a measuring instrument (1) for measuring and displaying the change of a characteristic property of a test element which correlates with the analyte and a lancing device (2) for obtaining blood from a body region of a test person, wherein the measuring instrument (1) and lancing device (2) are directly connected to one another in a detachable manner. In addition the invention concerns the use of such a system for determining the presence or the content of an analyte in blood.

20 Claims, 4 Drawing Sheets

ANALYTICAL MEASURING DEVICE WITH LANCING DEVICE

CROSS-REFERENCE TO RELATED APPLICATIONS

This a 371 of PCT/EP98/07706 filed Nov. 30, 1998.

BACKGROUND OF THE INVENTION

The invention concerns a system and its use for determining the presence or the content of an analyte in blood wherein the system comprises a measuring instrument for measuring and displaying the change of a characteristic property of a test element which correlates with the analyte and it concerns a lancing device for obtaining blood from a body region of a test person.

The determination of the content of a particular analyte in blood, for example glucose or lactate, requires the collection of an adequate amount of sample (blood) and the provision of a suitable measuring system for the analyte. In addition to medical practices and laboratories, medical laymen are increasingly carrying out such determinations for their own use. Measuring systems that are designed to be used by the test persons themselves are wide-spread especially for the determination and monitoring of the blood sugar value i.e. the blood glucose content in the case of diabetics and also to determine other parameters such as the lactate content or cholesterol level.

Conventional measuring systems often contain test elements in the form of so-called test strips which, together with appropriate measuring instruments, allow the determination of one or several analytes in the blood. In addition the user generally also requires a lancet which is used to pierce the skin of particular body regions for example of the finger pad or earlobe and thus obtain blood which is to be used for the measurement. Various manufacturers offer lancing devices for a comfortable blood collection which insert the lancets into the skin in a controlled and guided manner in order to thus control the piercing depth and to minimize the pain.

Since the user requires several separate components (test elements, measuring instrument, lancing device, lancets etc.) in order to measure an analyte in blood and has to carry them with him for an outside analysis for example when travelling or for sport, it is understandable that especially diabetics, which additionally have to carry insulin and a syringe, consider it desirable to reduce the individual components that they have to have with them.

There have therefore been no lack of various attempts at reducing the number of individual components. One solution is to package the necessary components such as measuring instrument, lancing device, lancets and test strips in a common transport case. However, these are often voluminous and for example too large and too heavy to be kept in a jacket or shirt pocket.

Another solution is to integrate as many of the above-mentioned components as possible into one instrument. An example of this is the integration of a test strip storage system into a measuring instrument as described in U.S. Pat. No. 5,489,414 or U.S. Pat. No. 5,645,798.

Systems in which the lancing device and measuring instrument have been amalgamated into one instrument are described for example in U.S. Pat. No. 5,029,583 and U.S. Pat. No. 4,637,403. Although these integrated systems essentially solve the problem of reducing the number of individual components that one has to carry, the handling of such integrated systems for blood collection is unsatisfactory since the systems are usually cumbersome and comparatively heavy and thus make it difficult to precisely aim at a lancing site.

The object of the present invention was to eliminate the disadvantages of the prior art. In particular the aim was to find a system which combines the measuring instrument and lancing device and allows a precise aiming at the lancing site with an overall reduction of the number of individual components that one has to carry.

SUMMARY OF THE INVENTION

The object is achieved by the subject matter of the invention as characterized in the patent claims.

The invention concerns a system for determining the presence or the content of an analyte in blood comprising a measuring instrument for measuring and displaying the change of a characteristic property of a test element which correlates with the analyte and a lancing device for obtaining blood from a body region of a test person characterized in that the measuring instrument and the lancing device are directly connected to one another in a detachable manner.

The invention also concerns the use of the system according to the invention to determine the presence or the content of an analyte in blood.

Finally the invention concerns the individual components of the system according to the invention i.e. a lancing device and a measuring instrument that are suitable for a direct detachable connection to one another.

The system according to the invention is suitable for the determination of the presence or the content of an analyte in blood. The determination of the presence of an analyte can for example be used for the qualitative diagnosis of an infection (e.g. with viruses such as HIV or HCV) or for the qualitative determination of a particular state of the body (e.g. pregnancy, cardiac infarction). The determination of the content of an analyte can be used to monitor the course of a disease or response to therapy and gives detailed information on the state of the body of a test person. Examples of this are the measurement of the blood glucose, the lactate or cholesterol concentration in the blood and such like. The system according to the invention preferably enables the determination of one parameter. The simultaneous determination of several parameters is also possible in a further embodiment of the system according to the invention.

According to the invention the measuring instrument of the system measures and displays the change of a characteristic property of a test element that correlates with the analyte. The test element can be present in any form that is well-known to a person skilled in the art for example in the form of a test strip or a cuvette where the reagents required for the detection reaction are present in or on the test element. When one or several analytes are present, the test element enables the generation of a detectable signal as a characteristic property of the test element which correlates with the analyte. Examples of this are colour changes in a detection reagent layer which can be measured photometrically, or electrical currents or changes in potential which can be detected by electrode systems. The signals generated in this manner are then measured and evaluated by the measuring instrument by for example comparison with calibration values. Different detection and determination methods are possible depending on the analyte to be examined which differ in the physicochemical detection principle (e.g. photometry, electrochemistry) and, on the other hand, in the bio(chemical) interactions which lead to the characteristic, detectable changes (e.g. detection by means of enzymatic or immunological reactions, nucleic acid sequence test).

In addition to the measuring instrument, the system according to the invention contains a lancing device which can be used to obtain a blood sample of a test person. Lancing devices are known for example to a person skilled in the art from EP-B 0 565 970 and are sold commercially in different forms by various vendors. They are used in combination with lancets to obtain blood for example from the finger pad or the earlobe in a comfortable, reproducible and painless manner.

In the claimed system the lancing device is connected according to the invention with the measuring instrument in a direct and detachable manner. Direct connection should be understood to mean that apart from the lancing device and the measuring instrument, no additional separate devices such as pockets, covers, tapes or cases are necessary to connect the lancing device and measuring instrument. In contrast the measuring instrument or the lancing device or both components contain appropriate connecting means which preferably match and fit one another and allow a detachable connection of the two components of the system. Possible connecting means are plug connections, clamp connections, connections using profiled rails, connections by means of magnets or Velcro fastenings. The connection is preferably by means of plug connections in which case a connection with the aid of a clip is particularly preferred.

The connection according to the invention between the lancing device and measuring instrument can be easily and rapidly detached and closed again and thus allows the system according to the invention to be handled comfortably which makes it more acceptable to the users.

Since in a preferred embodiment of the invention it should be equally possible to obtain blood of a test person by the lancing device in a detached state and also when connected to the measuring instrument, a stable connection has proven to be particularly advantageous i.e. a connection which resists the shear forces which are exerted on the connection during operation of the lancing device. A connection with the aid of a clip is particularly preferred. Clips are known in various shapes, materials and designs for example for writing utensils such as fountain pens, ball-point pens or felt-tip pens.

The clip is especially preferably attached to the lancing device which especially preferably has an essentially cylindrical, fountain-pen-like shape as in EP-B 0 565 970 and the measuring instrument which preferably essentially has the shape of a flat cuboid contains a recess with a corresponding shape particularly preferably on one of its narrow side faces which allows the clip to be held with an accurate fit and thus enables a stable, detachable and direct connection of the lancing device and measuring instrument. The clip and the corresponding recess to hold the clip are preferably shaped such that when the stable connecting position is reached, this is tactually or audibly discernible to the user. The combination of the clip on the lancing device and an essentially complementary recess in the housing of the measuring instrument enables an unequivocal, orientated and guided connection of the two system components according to the invention whereby the play between the lancing device and measuring instrument is optimized in order to create a stable connection which resists shear forces and, on the other hand, can be easily and rapidly detached. The lancing device particularly preferably ends up essentially resting against the narrow side of the measuring instrument as a result of its connection with the measuring instrument.

The lancing device and housing of the measuring instrument are preferably designed such that a compact overall shape results. For example a recess in the shape of a trough which at least partially encloses the lancing device can be provided in the housing of the measuring instrument. In addition to the compactness of the arrangement, this also additionally stabilizes the detachable connection between the lancing device and measuring instrument.

The clip for connecting the lancing device and measuring instrument can be manufactured from the housing material of the lancing device or of the measuring instrument as well as from another suitable material. Suitable materials are for example metals, alloys or plastics or combinations thereof e.g. plastic-coated metals or metallized plastics. The clip can be a component of the housing which is for example manufactured as an injection moulded part or it can be a separate component which is, however, permanently connected to the housing.

It has also turned out that the lancing device and measuring instrument can be also advantageously connected by the shaping of the measuring instrument housing. For example the measuring instrument can contain a flexible gripping jaw on one, preferably narrow side of the housing which partially encloses the lancing device and thus enables it to be detachably attached to the measuring instrument. In this case it is not necessary to attach devices to the lancing device to attach it to the measuring instrument. In this preferred embodiment the means for detachably connecting the lancing device and measuring instrument can be an integral component of the housing of the measuring instrument and can for example be incorporated into it during the injection moulding process. However, the said means can also be moulded as a separate component that is, however, permanently connected to the housing.

The system according to the invention provides the user with a compact lancing device-measuring instrument system which reduces the number of individual components that the user needs to obtain blood and subsequently measure a blood parameter. An additional advantage is that the user can decide whether he wants to use the lancing device connected to the measuring instrument or detached from the measuring instrument which enables a high degree of flexibility in operation. Moreover the lancing device can be cleaned safely and hygienically without a risk of damaging the measuring instrument.

BRIEF DESCRIPTION OF THE DRAWINGS

The invention is elucidated in more detail by the following FIGS. 1 to 5.

Figure 1:
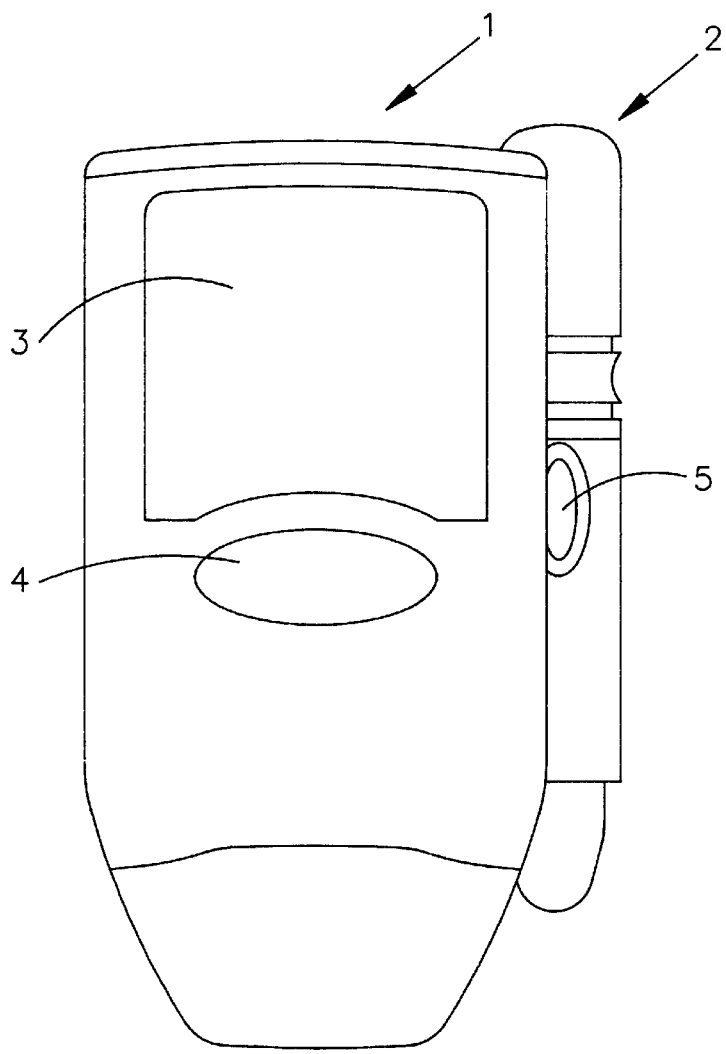
FIG. 1 shows schematically a top-view from above of a preferred embodiment of the system according to the invention.

The numbers in the figures denote:
1 measuring instrument
2 lancing device
3 display
4 operating element for the measuring instrument
5 operating element for the lancing device
6 connecting element 1 (clip)
7 connecting element 2 (complementary recess)
8 housing wall of the measuring instrument 1
9 clamping jaw

DESCRIPTION OF PREFERRED EMBODIMENTS

Figure 2:
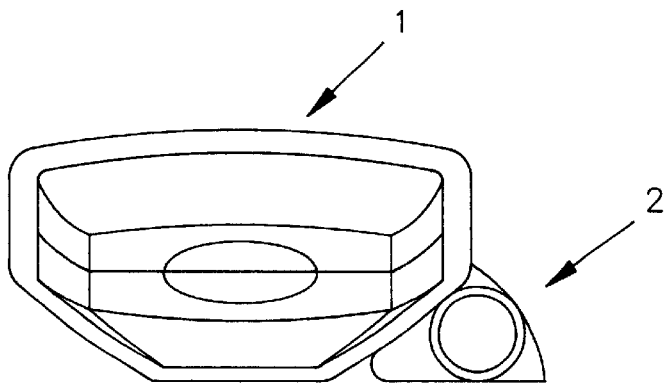
FIG. 2 is a schematic top-view from direction A of the system according to the invention shown in FIG. 1.
Figure 3:
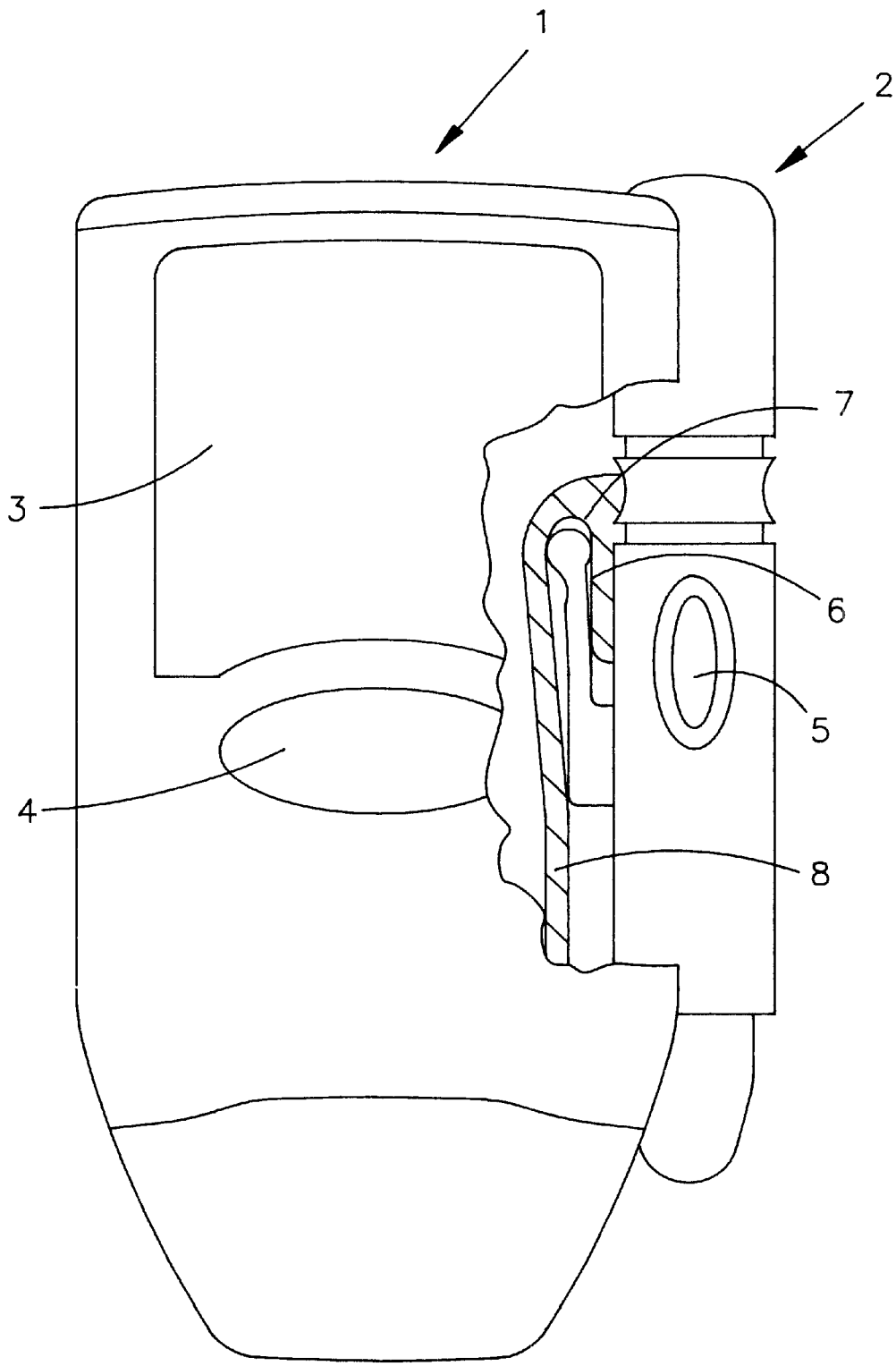
FIG. 3 shows schematically the connecting mechanism for the lancing device and measuring instrument of the system according to the invention of FIG. 1 on the basis of a partial sectional view.

The system shown in FIGS. 1 to 3 which represents a particularly preferred embodiment of the invention is composed of a measuring instrument 1 and a lancing device 2 which are connected directly and detachably to one another. In this case the lancing device 2 ends up resting essentially against the side of the measuring instrument 1.

The dimensions of the measuring instrument 1 are preferably such that it can be held comfortably in one hand. The lancing device 2 has essentially the shape of a fountain pen and its size (length, diameter) is essentially matched to the measuring instrument 1 in such a way that no overhanging or protruding parts are present for the transport and operation of the system.

The measuring instrument 1 contains all necessary functional components of which only the display 3 and an operating element 4 are shown schematically in FIGS. 1 and 3. The test elements which are to be measured with the measuring instrument 1 are inserted into the instrument 1 from side A in FIG. 1 or, alternatively to instrument 1, can for example be provided by an integrated test element magazine.

The lancing device 2 also contains all necessary functional components of which only an operating element 5 is shown schematically. The lancets for obtaining blood are inserted into the lancing device 2 from side A (FIG. 1).

FIG. 3 shows a schematic detailed view of the connecting elements 1 (clip) 6 and 2 (complementary recess) 7 for which a part of the upper side of the measuring instrument has been left out. The clip 6 fits exactly into the complementary recess 7 which is formed by the wall of the housing 8 of the measuring instrument 1.

When using the lancing device 2 the operator will usually detach it from the measuring instrument 1 in order to collect blood as precisely and painlessly as possible. For this purpose a corresponding lancet has to be inserted into the lancing device 2, the lancing device 2 is activated by for example tensioning a spring and is subsequently moved to the desired body region such as a finger pad or earlobe from which it is intended to draw the blood. When the operating element 5 is actuated, the lancet pierces the desired body region and thus blood is obtained.

The blood is subsequently applied to the sample application region of a test element which is preferably already located in the measuring instrument 1 and at least the sample application region of the test element protrudes from the measuring instrument 1. The actual measurement is started by actuating the operating element 4. After the detection reaction is completed on the test element the measured value of the analyte determination appears in the display 3.

In the other preferred embodiment of the system according to the invention shown in FIG. 4 which is composed of lancing device 2 and measuring instrument 1, the detachable connection between these two system components is also accomplished by a clip 6 on the lancing device 2 and a corresponding complementary recess 7 on the measuring instrument 1. The recess 7 is located in a side wall of the measuring instrument housing which matches the contours of the lancing device in order to stabilize the connection between the measuring instrument 1 and lancing device 2.

Figure 4B:
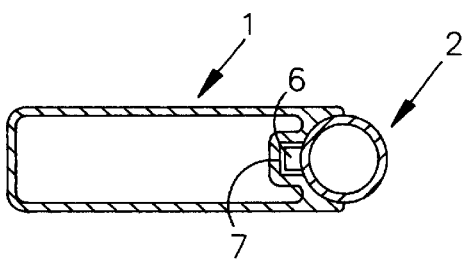
FIG. 4 shows a preferred embodiment of the system according to the invention as an alternative to FIGS. 1 to 3 based on three partial figures (A to C).
Figure 4C:
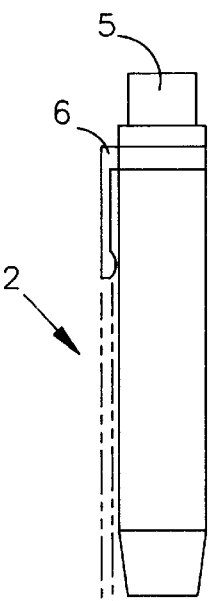
Figure 4C:
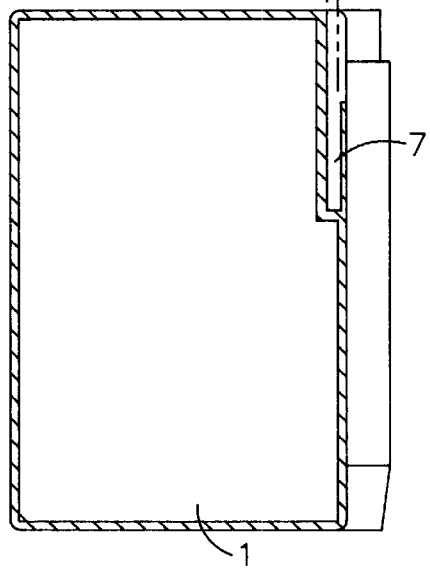
Figure 4A:
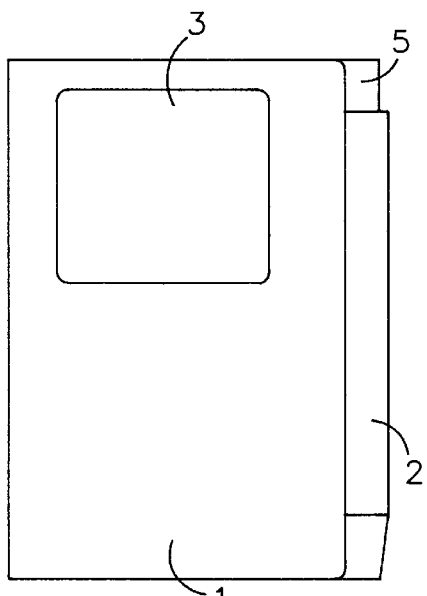

The top-view in FIG. 4A shows the locations of the measuring instrument 1 and lancing device 2 in the connected state. FIG. 4B is a section through the plane of measuring instrument 1 and lancing device 2 indicated by the arrows in FIG. 4A. This cross-section shows well how the side wall of the measuring instrument housing matches the contour of the lancing device 2.

FIG. 4C illustrates how the lancing device 2 docks with the measuring instrument 1. The lancing device 2 is orientated parallel to the measuring instrument 1 with the clip 6 facing the side of the housing which contains the recess 7 that is complementary to the clip 6 and the lancing device is connected to the measuring instrument 1 by inserting the clip 6 into the recess 7. Clip 6, recess 7 and the matching of the side wall of the measuring instrument 1 to the lancing device 2 ensure that the connection is stable but can be detached again. The connection is detached in the reverse sequence to making the connection.

Figure 5C:
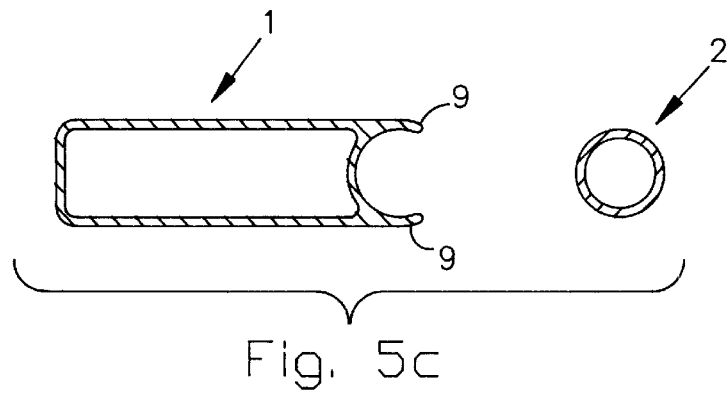
FIG. 5 also shows a preferred embodiment of the system according to the invention as an alternative to FIGS. 1 to 4 which is also based on three partial figures (A to C).
Figure 5B:
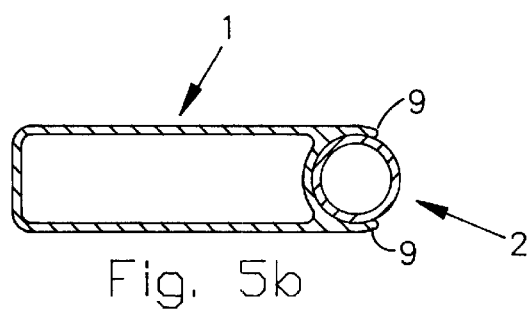

FIG. 5 finally shows an alternative connecting mechanism for the lancing device 2 and measuring instrument 1. In this case the lancing device 2 contains no special devices which allow a connection to the measuring instrument but rather the connection is made by a special shape of one of the side walls of the housing of the measuring instrument 1. This wall of the housing contains clamping jaws 9 which in the preferred embodiment of the lancing device 2 shown that has a round cross-section (FIG. 5B and C) partially surround it and hold it in such a way that it can be readily detached. The material from which the jaws 9 are made is on the one hand flexible enough so that it can be pressed apart to hold the lancing device 2 and on the other hand is stiff enough that it fixes the lancing device 2 once it has been partially surrounded by the jaws 9 and rests against the measuring instrument 1.

Figure 5A:
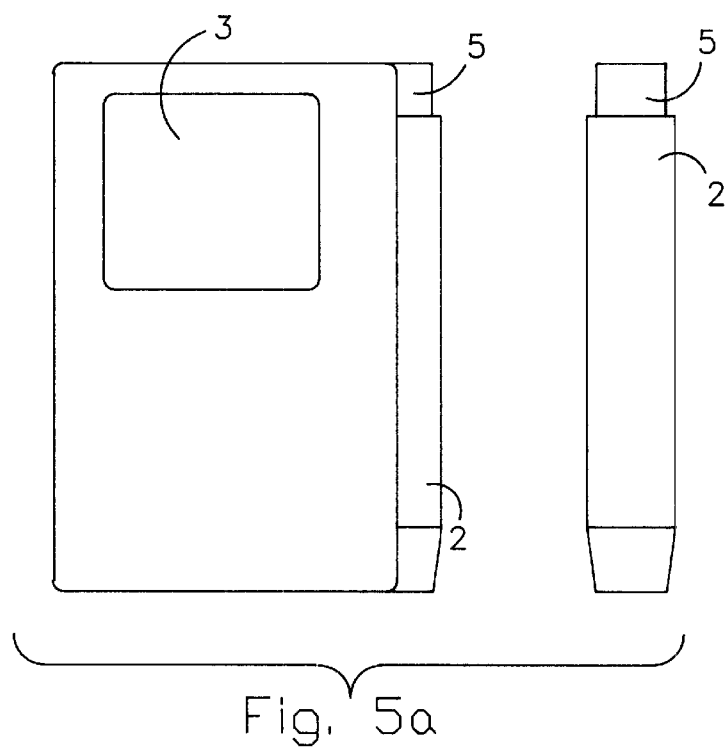

FIG. 5A shows in a top-view how the lancing device 2 approaches the measuring instrument 1 and is held by the clamping jaws 9 on the measuring instrument 1. A schematic section through the plane of the measuring instrument 1 and lancing device 2 indicated by the arrows in FIG. 5A is shown in FIG. 5B. In this cross-section it can be readily seen how the clamping jaws 9 are components of the housing wall of the measuring instrument 1 which surround the lancing device 2. FIG. 5C is like FIG. 5B a schematic cross-section through the lancing device 2 and measuring instrument and in this case the arrows are intended to illustrate how the jaws 9 of the measuring instrument housing move apart when the lancing device 2 is inserted.

What is claimed is:
1. A system for determining the presence or content of an analyte in blood, the system comprising a photometric or electrochemical measuring instrument for measuring and displaying the change of a characteristic property of a test element which correlates with the analyte, the measuring instrument being enclosed in an instrument housing, and a lancing device, including an outer surface, for obtaining blood from a body region of a test person, wherein the measuring instrument housing and the lancing device outer surface are directly and detachably connected to one another so that blood can be obtained from a body region of a test person with the aid of the lancing device when the lancing device outer surface is connected to the measuring instru- ment housing as well as when the lancing device is detached from the measuring instrument.

2. The system of claim 1 wherein the lancing device outer surface includes a protruding clip, and the measuring instrument housing includes a corresponding recess adapted to receive the clip.

3. The system of claim 2 wherein the clip is an integral component of the lancing device outer surface.

4. The system of claim 2 wherein the clip is a separate component from the lancing device outer surface that is permanently fixed to the outer surface.

5. The system of claim 1 wherein a side of the measuring instrument housing includes a trough, and the lancing device is detachably connected in the trough on the side of the measuring instrument.

6. The system of claim 5 wherein the trough comprises a flexible gripping jaw for partially enclosing the lancing device.

7. The system of claim 2 wherein the flexible gripping jaw is an integral component of the measuring instrument housing.

8. The system of claim 6 wherein the flexible gripping jaw is a separate component from the measuring instrument housing that is permanently fixed to the measuring instrument housing.

9. The system of any of claims 1–5 wherein the lancing device outer surface has a cylindrical, fountain pen-like form.

10. The system of claim 1 further comprising apparatus on the measuring instrument housing and the lancing device outer surface which enable the measuring instrument and the lancing device to be connected detachably.

11. The system of claim 1, 2 or 10 wherein said measuring instrument includes at least one element for tactually or audibly indicating that a stable connection has been achieved between the measuring instrument housing and the lancing device outer surface.

12. The system of claim 1, 2 or 10 wherein the measurement instrument housing at least partially encloses the lancing device when a stable connection has been achieved between the measuring instrument housing and the lancing device outer surface.

13. A lancing device suitable for use in the system of claim 1 wherein the lancing device outer surface is designed such that the lancing device can directly and detachably connect to a measuring instrument housing for measuring and displaying the change of a characteristic property of a test element which correlates with the analyte.

14. A measuring instrument suitable for use in the system of claim 1 wherein the measuring instrument housing is designed such that the measuring instrument housing can directly and detachably connect to a lancing device for obtaining blood from a body region of a test person.

15. A system for determining the presence or content of an analyte in a body fluid, the system comprising a photometric or electrochemical measuring instrument for measuring and displaying the change of a characteristic property of a test element subjected to the body fluid which correlates with the analyte, the measuring instrument being enclosed in an instrument housing, and a lancing device, including an outer surface, for obtaining the body fluid from a body region of a test person, wherein the measuring instrument housing and the lancing device outer surface are directly and detachably connected to one another, the measurement instrument housing at least partially enclosing the lancing device and including at least one element for tactually or audibly indicating that a stable connection has been achieved between the measuring instrument housing and the lancing device outer surface.

16. The system of claim 15 wherein the lancing device outer surface includes a protruding clip, and the measuring instrument housing includes a corresponding recess adapted to receive the clip.

17. The system of claim 16 wherein the lancing device outer surface defines a generally elongated structure having a longest dimension in a longitudinal direction, the protruding clip being received in the corresponding recess by movement of the lancing device relative to the measuring instrument housing in the longitudinal direction.

18. The system of claim 15 wherein a side of the measuring instrument housing includes a trough, and the lancing device is detachably connected in the trough on the side of the measuring instrument.

19. The system of claim 16 wherein the lancing device outer surface defines a generally elongated structure having a longest dimension in a longitudinal direction, the lancing device being received in the trough by movement of the lancing device relative to the measuring instrument housing in a direction normal to the longitudinal direction.

20. The system of any of claims 15–19 wherein the lancing device outer surface has a cylindrical, fountain pen-like form.

* * * * *